United States Patent [19]
Southwell

[11] Patent Number: 4,707,611
[45] Date of Patent: Nov. 17, 1987

[54] INCREMENTAL MONITORING OF THIN FILMS

[75] Inventor: William H. Southwell, Thousand Oaks, Calif.

[73] Assignee: Rockwell International Corporation, El Segundo, Calif.

[21] Appl. No.: 939,499

[22] Filed: Dec. 8, 1986

[51] Int. Cl.[4] ............................................. G01B 11/02
[52] U.S. Cl. .................................... 250/560; 250/571; 356/382
[58] Field of Search ........................ 250/559, 560, 571; 356/381, 382; 364/563

[56] References Cited

U.S. PATENT DOCUMENTS

3,896,211  3/1975  Watanab et al. ..................... 356/381
4,453,828  6/1984  Hershel et al. ...................... 356/381

FOREIGN PATENT DOCUMENTS

58-90148  5/1983  Japan .................................. 356/382

OTHER PUBLICATIONS

Berning, Use of Equivalent Films in Design of Infrared Multilayer Antireflection Coatings, Journal of Optical Society of America, vol. 52, p. 431 (1962).
Budde, Photoelectric Analysis of Polarized Light, Applied Optics, vol. 1, p. 201 (1962).
Dobrowolski, Completely Automatic Synthesis of Optical Thin Film Systems, Applied Optics, vol. 4, p. 937 (1965).
Epstein, The Design of Optical Filters, Journal of the Optical Society of America, vol. 42, p. 806 (1952).
Hauge, et al., Design and Operation of ETA, an Automated Ellipsometer, IBM Journal of Research & Development, p. 472 (Nov. 1973).
Hottier, et al., In Situ Monitoring by Ellipsometry of Metalorganic Epitaxy of GaAlAs–GaAs Superlattice, J. Applied Physics, vol. 51, p. 1599 (1980).

(List continued on next page.)

Primary Examiner—Edward P. Westin
Assistant Examiner—Khaled Shami
Attorney, Agent, or Firm—H. Fredrick Hamann; Craig O. Malin; John J. Deinken

[57] ABSTRACT

The thickness t and refractive index n of an incremental thin film layer deposited on a base stack of layers are determined, where the characteristic matrix M of the base stack is $$M = \begin{pmatrix} M_{11} & iM_{12} \\ iM_{21} & M_{22} \end{pmatrix},$$

by directing light at a first wavelength toward the layer and the base stack, measuring the reflectance of the first wavelength light from the layer and the base stack, directing light at a second wavelength toward the layer and the base stack, and measuring the reflectance of the second wavelength light from the layer and the base stack. The measured values of reflectance for each wavelength are then substituted in the relationship $$\text{reflectance} = \frac{(B_1 - C_1)^2 + (B_2 - C_2)^2}{(B_1 + C_1)^2 + (B_2 + C_2)^2}$$

where $B_1 = M_{11}\text{Cos}\phi - (M_{21}/n)\text{Sin}\phi,$ $B_2 = N_s(M_{12}\text{Cos}\phi + (M_{22}/n)\text{Sin}\phi),$ $C_1 = N_s(M_{22}\text{Cos}\phi - M_{12}n\text{Sin}\phi),$ $C_2 = M_{11}n\text{Sin}\phi + M_{21}\text{Cos}\phi,$ $\phi = 2\pi nt/\lambda,$ $N_s$ is the refractive index of the substrate, and
$\lambda$ is the wavelength at which the reflectance is measured.

The thickness t and the refractive index n are determined by solving the two reflectance equations.

12 Claims, 2 Drawing Figures

OTHER PUBLICATIONS

Minot, Single-Layer, Gradient Refractive Index Antireflection Films Effective from 0.35 to 2.5μ, J. of Optical Society of America, V. 66, p. 515 (1976).

Netterfield, et al., Characterization of Growing Thin Films by in situ Ellipsometry, Spectral Reflectance and Transmittance Measurements, and Ion-Scattering Spectroscopy, Review of Scientific Instruments, vol. 56, p. 1995 (1985).

Snedaker, New Numerical Thin-Film Synthesis Technique, Journal of the Optical Society of America, vol. 72, p. 1732 (1982).

Southwell, Quintic Refractive Index Profile Antireflection Coatings, U.S. Pat. No. 4,583,822.

Southwell, Gradient-Index Antireflection Coatings, Optics Letters, vol. 8, p. 584 (1983).

Southwell, Coating Design Using Very Thin High- and Low-Index Layers, Applied Optics, vol. 24 (1985).

Theeten, Ellipsometric Assessment of (Ga,Al) As/GaAs Epitaxial Layers During their Growth in an Organometallic VPE System, Journal of Crystal Growth, vol. 46, p. 245 (1979).

Yadava, Optical Behavior of Gradient-Index Multilayer Films, Thin Solid Films, vol. 21, p. 297 (1974).

INCREMENTAL MONITORING OF THIN FILMS

GOVERNMENT RIGHTS

The United States Government has rights in this invention pursuant to a contract awarded by the Department of the Army.

BACKGROUND OF THE INVENTION

This invention is concerned with the deposition of multiple layer optical thin films and, in particular, with techniques for continuously monitoring the thickness and refractive index of each layer in such films as it is deposited.

Optical films are of practical importance because they can be used to control the reflecting and transmitting properties of an optical system. A nonreflecting film, for example, can substantially reduce the loss of light by reflection at the various surfaces of a multielement camera lens. Stray light, which could otherwise reach the image because of these reflections, can also be substantially eliminated, with a resulting increase in contrast. Such improvements are particularly useful where an image is formed by a highly corrected lens system which employs a large number of interfaces between air and glass. Consequently, almost all optical components of high quality are equipped with thin film coatings to reduce reflection.

Thin optical films depend on the phenomenon of optical interference, which causes the intensities of transmitted and reflected light to be modified when two or more beams of light are superimposed. If a film of a transparent substance is deposited on glass, for example, with an optical thickness which is equal to one fourth the wavelength of a particular frequency of light, the reflection of that light from the glass surface can be almost completely suppressed by the quarter-wave layer. The light which would otherwise be reflected is not absorbed by a nonreflecting film; rather, the energy in the incident light is redistributed so that a decrease in reflection is accompanied by a concomitant increase in the intensity of the light which is transmitted.

Considerable improvements have been achieved in the antireflective performance of optical thin films by using composite films having two or more superimposed layers. The use of gradient index layers, in which the index of refraction within a layer is made to vary continuously as a function of depth in the layer, further increases the degrees of freedom available in the design of such films. In addition to these techniques, advanced optical thin film design procedures, which involve theoretically predicting the required refractive index profile for any desired transmission or reflection spectrum, have been instrumental in the development of a wide range of new optical devices whose performance is enhanced by spectrally complex filter structures. A rugate filter, for example, utilizes a gradient-index structure with a sinusoidal refractive index profile. The optical properties of the filter are determined by the values of $n_a$, the average refractive index, and $n_p$, the index modulation. As for quarter-wave reflectors, the width of the reflection band for such a filter is proportional to $(n_p/n_a)$, while the peak value of the reflectance is determined by $N(n_p/n_a)$ where N is the number of sinusoidal periods in the filter. High reflectivity can thus be maintained within a narrow bandwidth by increasing the number of periods in the rugate filter structure.

Practical realizations of rugate and other gradient index thin film structures, however, have been inhibited by the limitations of thin film fabrication technology. A highly accurate technique is needed to monitor in-situ the thickness and refractive index of the layers in these complex structures during the deposition process. Rugate filters, for example, have an allowable thickness error during deposition of no more than 1% of a layer's thickness. A slight change in the thickness of a single layer will introduce a phase shift which can have a significant detrimental effect on the filter spectral structure. Moreover, errors in refractive index within a deposition cycle will add additional frequency components to the profile, resulting in the growth of unwanted sidebands in the transmittance or reflectance spectrum of the filter. It is very difficult to compensate for such perturbations by the subsequent deposition of accurately fabricated layers. Consequently, precise monitoring of the deposition process is an absolute necessity.

The standard optical reflectance quarter-wave monitoring techniques of the prior art yield only the thickness of a deposited layer or, at best, the thickness and index of relatively thick layers deposited on known substrates. Generating gradient-index films with these prior art methods requires an exceptionally large number of monitor substrates. Consequently these conventional measurement methods have been found unsuitable to ensure the accurate deposition of complex gradient-index structures. A need has thus developed in the art for a monitoring method for these advanced thin film deposition processes which will measure the film thickness and refractive index without exhibiting the disadvantages of the standard methods.

SUMMARY OF THE INVENTION

The thickness t and refractive index n of an incremental thin film layer deposited on a base stack of layers are determined, where the characteristic matrix M of the base stack is $$M = \begin{pmatrix} M_{11} & iM_{12} \\ iM_{21} & M_{22} \end{pmatrix},$$

by directing light at a first wavelength toward the layer and the base stack, measuring the reflectance of the first wavelength light from the layer and the base stack, directing light at a second wavelength toward the layer and the base stack, and measuring the reflectance of the second wavelength light from the layer and the base stack. The measured values of reflectance for each wavelength are then substituted in the relationship $$\text{reflectance} = \frac{(B_1 - C_1)^2 + (B_2 - C_2)^2}{(B_1 + C_1)^2 + (B_2 + C_2)^2}$$

where $B_1 = M_{11} \cos\phi - (M_{21}/n) \sin\phi$, $B_2 = N_s(M_{12} \cos\phi + (M_{22}/n) \sin\phi)$, $C_1 = N_s(M_{22} \cos\phi - M_{12}n \sin\phi)$, $C_2 = M_{11}n \sin\phi + M_{21} \cos\phi$, $\phi = 2\pi nt/\lambda$, $N_s$ is the refractive index of the substrate, and $\lambda$ is the wavelength at which the reflectance is measured. The thickness t and the refractive index n are determined by solving the two reflectance equations.

In a more particular embodiment, the first and second wavelengths of light are selected to be no more than four times the optical thickness of the incremental layer.

In another more particular embodiment, the light is directed normal to the surface of the layer.

The invention also contemplates a method of monitoring the thickness t and refractive index n of a thin film layer as the layer is deposited on a base stack of layers. The thickness t and the refractive index n are again determined by solving the two reflectance equations. The characteristic matrix M is then updated to include the layer. The steps of directing, measuring, deriving, and updating are repeated at predetermined increments during the growth of the layer.

The accuracy of the thickness measurement may be ensured by selecting the first and second wavelengths of light to be no more than four times the optical thickness of each measured layer or by selecting the predetermined measurement increments so that the optical thickness of each measured layer is at least one fourth as large as the first and second wavelengths of light.

In another embodiment, the invention is an improved method of making a multiple thin film optical coating which is effective at an operational wavelength, the method including the steps of calculating the desired thickness and index of refraction for each layer in the coating and depositing each layer while continuously monitoring the thickness and index of the layer. The improvement involves monitoring the thickness and refractive index by measuring the reflected light at two wavelengths and solving the two reflectance equations.

DESCRIPTION OF THE INVENTION

It is an outstanding feature of this invention to provide a new technique for in-situ, real-time monitoring during the deposition of an optical thin film layer. With this technique, reflectance measurements are obtained using two or more different wavelengths of light and are used to calculate the film thickness and index of incremental layers as those layers are deposited on top of a base stack configuration. Since both the thickness and the refractive index of an incremental layer can be determined, the present invention allows the deposition rates of co-evaporated films to be controlled so that gradient-index films can be produced.

Figure 1:
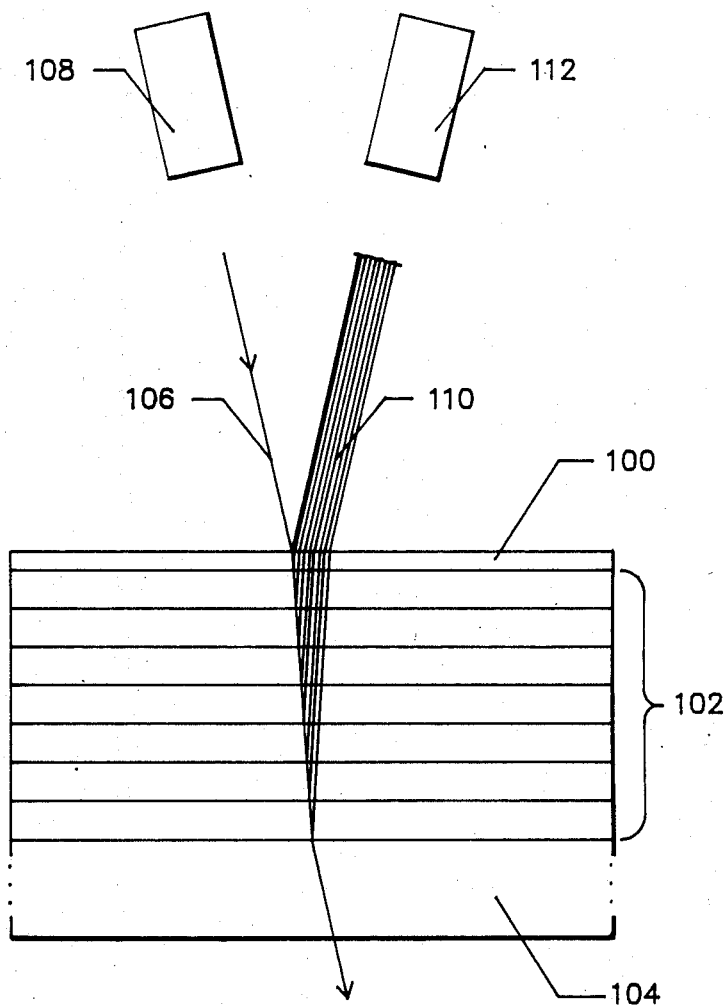
FIG. 1 is a schematic drawing illustrating the technique of this invention as applied during the deposition of a multiple thin layer optical coating.

A multiple thin film optical coating is created by first calculating the proper thickness and index of refraction for each layer in the coating according to the operational wavelength at which the coating is to be effective and the desired reflectance or transmittance profile of the coating. Each layer is then deposited to the specified thickness using materials which provide the proper refractive index. These steps of calculating the layer specifications and depositing the layers are not further described here since they can be accomplished by a number of techniques known to those skilled in the art. FIG. 1 is a schematic drawing illustrating the technique of this invention as it is applied to a thin film layer during the deposition of a multiple layer optical coating. A thin film layer 100 is being deposited on a base stack of layers 102, the base stack having been deposited on a substrate 104. Light 106 at a first wavelength is obtained from a source 108 and directed toward the deposited layers. The light 106 is shown directed at an oblique angle with respect to the surface of the layer in order to maximize the illustrative value of the drawing. Those skilled in the art, however, will recognize that in the preferred embodiment of this technique the light is directed normal to the surface of the layer. The light 106 is divided into reflected and transmitted portions as it traverses each interface between the thin film layers. The reflected portions 110 of the light eventually emerge from the layers and are received by a detector 112, which measures the reflectance. These steps of directing light at the layer and measuring the reflectance are then repeated for light at a second wavelength. The thickness and refractive index of the layer 100 are estimated by substituting the measured reflectance values for each wavelength into equations relating the reflectance to the thickness and refractive index, as explained below. This technique can be used to continuously monitor the thickness and refractive index of a layer as the layer is deposited by repeating the technique at predetermined intervals during the growth of the layer. The measured thickness and index values are used to determine when to terminate the growth of a particular layer or to change the layer materials to adjust the refractive index of the layer, as required by the predetermined layer profile for the coating.

Incremental monitoring analysis utilizes to the fullest the characteristic matrix theory of multilayer thin films. This theory states that any multilayer stack may be represented, as to its effect on a given wavelength of light traversing the stack, by a single 2 by 2 matrix, regardless of the layer thickness. Even an arbitrary gradient-index coating can be represented by a 2 by 2 matrix, since any such configuration may be broken down into many thin homogeneous layers. Furthermore, this matrix is independent of the substrate on which the multilayer stack is deposited and is independent of the incident media through which the light travels. Perhaps the most powerful attribute of the characteristic matrix method as applied to incremental monitoring is that the matrix which characterizes the base stack can be readily updated to account for an additional layer by performing a simple 2 by 2 matrix multiplication. Thus the history of the previously deposited layers in a multilayer stack is always contained in the updated base stack matrix and is used to update the matrix as each additional layer is added.

The base stack configuration of dielectric layers is represented, for a given wavelength of light, by the matrix:

$$M = \begin{pmatrix} M_{11} & iM_{12} \\ iM_{21} & M_{22} \end{pmatrix}, \tag{1}$$

where $M_{11}$, $M_{12}$, $M_{21}$, and $M_{21}$ are the elements of the matrix and i is the imaginary unit $\sqrt{-1}$. See Epstein, The Design of Optical Filters, Journal of The Optical Society of America, Volume 42, Page 806 (1952); Macleod, Thin-Film Optical Filters, Pages 32–35 (Macmillan 1986). The matrix for a homogeneous film of index n and geometrical thickness t is:

$$M = \begin{pmatrix} \cos\phi & (i/n)\sin\phi \\ i\,n\sin\phi & \cos\phi \end{pmatrix} \quad (2)$$

where $\phi$ is the optical thickness of the film, given by $\phi = 2\pi nt/\lambda$, where $\lambda$ is the wavelength at which the reflectance is measured. Initially, before any deposition occurs on an uncoated substrate, M is the identity matrix; i.e., $M_{11} = M_{22} = 1$ and $M_{12} = M_{21} = 0$. The reflectance R from this base stack is a function of the thickness and index of an incremental layer deposited on the base stack:

$$R = \left| \frac{B - C}{B + C} \right| \quad (3)$$

where $$\begin{pmatrix} B \\ C \end{pmatrix} = \begin{pmatrix} \cos\phi & (i/n)\sin\phi \\ i\,n\sin\phi & \cos\phi \end{pmatrix} \begin{pmatrix} M_{11}\ iM_{12} \\ iM_{21}\ M_{22} \end{pmatrix} \begin{pmatrix} 1 \\ N_s \end{pmatrix} \quad (4)$$

where $N_s$ is the index of the substrate. Applying some matrix multiplication to Equation (3) yields:

$$B = B_1 + iB_2 \quad (5)$$
$$= (M_{11}\cos\phi - M_{21}/n\,\sin\phi) + iN_s(M_{12}\cos\phi + M_{22}/n\,\sin\phi)$$

$$C = C_1 + iC_2$$
$$= N_s(M_{22}\cos\phi - M_{12}N\sin\phi) + i(M_{11}N\sin\phi + M_{21}\cos\phi)$$

so that the reflectance R may be expressed as:

$$R = \frac{(B_1 - C_1)^2 + (B_2 - C_2)^2}{(B_1 + C_1)^2 + (B_2 + C_2)^2} \quad (6)$$

Equation (6) is used in this invention for estimating the thickness and index of the incremental layer. R is a function of M11, M12, M21, M22, and $N_s$, all of which are known, and t and n, the unknown thickness and index of the incremental layer. Thus two reflectance measurements at two different wavelengths will yield two equations involving two unknowns, t and n. This system of equations can then be solved to determine the thickness and refractive index values.

The thickness and refractive index are monitored by beginning with the known characteristic matrix at each wavelength for the bare substrate. Then the reflectance of light from the layer stack is measured for each wavelength at increments during the deposition of the layer. The thickness of the incremental layer which accumulates between measurements must be thin enough that the index of refraction can be assumed to be constant throughout the layer. After each set of measurements is taken, values for the thickness n and the refractive index t are derived from the measured values of reflectance and the relationship given in Equation (6). Once the index and thickness of the incremental layer are calculated, the base stack matrix for each wavelength is updated by multiplying the two 2 by 2 matrices in Equation (3). This measuring and updating sequence is repeated at suitable intervals throughout the deposition process, so that each layer's thickness and refractive index are determined at each increment from a known base stack. The technique produces a single index estimate, which may be an average or effective index, for the incremental layer. This approach improves accuracy and provides a means for the index profile to be precisely controlled according to the desired profile for the multilayer film.

Figure 2:
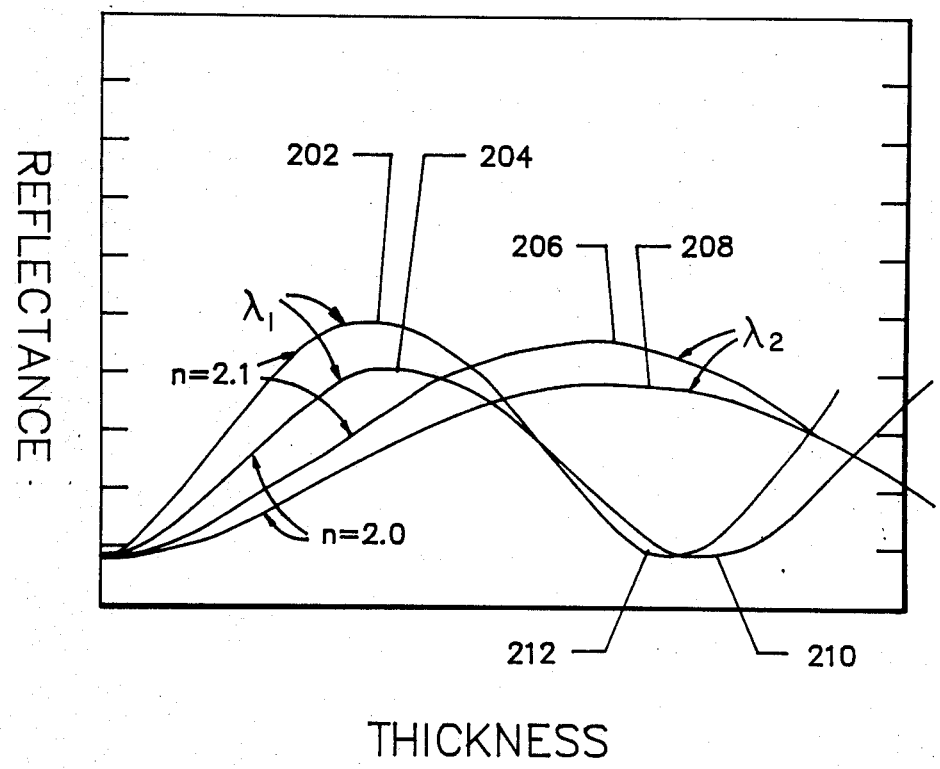
FIG. 2 is a graphical plot generated to predict the reflectance as a function of the thickness of a hypothetical thin layer at two wavelengths of light $\lambda_1$ and $\lambda_2$ and for a layer having two different values of the incremental refractive index.

FIG. 2 is a graphical plot which was generated to predict the reflectance as a function of the thickness of a hypothetical thin layer at two wavelengths of light $\lambda_1$ and $\lambda_2$ and for a layer having two different values of the incremental refractive index n (n=2.0 and n=2.1). The plot illustrates that, except at the turning points (e.g., thicknesses corresponding to points 202, 204, 206, 208, 210, and 212), where the change in reflectance with respect to thickness is 0, an absolute reflectance measurement will determine the thickness of the layer. Selecting a different wavelength of light for a second measurement of reflectance will avoid the ambiguity at a turning point, except near zero thickness on a bare substrate, which is a turning point at all wavelengths. Furthermore, the trajectory of reflectance measurements versus thickness for a new layer deposited on a fresh substrate will begin the same, regardless of the index of the layer. Consequently, the optical thickness of a layer (the product of the actual thickness of the layer and the refractive index of the layer) must reach a threshold thickness before the change in reflectance will be sufficient to monitor the thickness. A suitable threshold thickness, for example, might be at least one tenth of a quarterwave for the light used to make the measurement. Making two reflectance measurements at two different wavelengths enables both the thickness and the index of refraction of the incremental layer to be determined.

Another problem can occur because of the lack of uniqueness of the measured data, i.e., there may be a family of solutions for a given set of reflectance values. With very small errors in the reflectance data, the estimates for t and n could thus be far from the correct values. This ambiguity can be ameliorated by making reflectance measurements at more than two wavelengths, by using thicker incremental layers, or by assuming a constant deposition rate and correlating the reflectance measurements to time. In the latter approach, the reflectance measurements will be proportional to the thickness of the layer if the deposition rate is known. The sensitivity to reflectance measurement errors may be dramatically reduced if the incremental layer thickness is kept greater than a quarterwave optical thickness for the shortest monitoring wavelength which is used. Adhering to this constraint ensures that a reflectance turning point will be included in each incremental layer data set. A gradient-index coating designed to be effective at 10 microns, for example, could be deposited with one monitoring wavelength as small as 0.5 microns. Thus an incremental layer as thin as 0.125 microns could be accurately measured. Another desirable quality of the finished coating is that its layers be sufficiently thin that the coating behaves like a continuous gradient-index coating at the operational wavelength. This attribute can be ensured by selecting the measurement increments so that the optical thickness of each measured layer is no more than 1/40 of the operational wavelength for the coating. In the above example, a layer thickness of 0.125 microns corresponds to only 1/80th of a wavelength at the 10 micron operational wavelength. This 1/80th fraction is small enough that the resulting stepped index gradient-index coating will behave like a continuous gradient-index coating.

The preferred embodiment of this invention has been illustrated and described above. Modifications and additional embodiments, however, will undoubtedly be apparent to those skilled in the art. Although the preferred embodiments, for example, have been described using this technique to make both thickness and index of refraction measurements, the technique is also useful for making accurate thickness measurements where the index is known. Furthermore, equivalent elements may be substituted for those illustrated and described herein, parts or connections might be reversed or otherwise interchanged, and certain features of the invention may be utilized independently of other features. Consequently, the exemplary embodiment should be considered illustrative, rather than inclusive, while the appended claims are more indicative of the full scope of the invention.

I claim:

1. A method of determing the thickness t and refractive index n of an incremental thin film layer deposited on a base stack of layers, the base stack having a known characteristic matrix M of the form $$M = \begin{pmatrix} M_{11} & iM_{12} \\ iM_{21} & M_{22} \end{pmatrix},$$

comprising the steps of:
directing light at a first wavelength toward the layer and the base stack;
measuring the reflectance of the first wavelength light from the layer and the base stack;
directing light at a second wavelength toward the layer and the base stack;
measuring the reflectance of the second wavelength light from the layer and the base stack;
substituting the measured values of reflectance for each wavelength in the relationship $$\text{reflectance} = \frac{(B_1 - C_1)^2 + (B_2 - C_2)^2}{(B_1 + C_1)^2 + (B_2 + C_2)^2}$$

where $B_1 = M_{11} \cos \phi - (M_{21}/n) \sin \phi,$ $B_2 = N_s(M_{12} \cos \phi + (M_{22}/n) \sin \phi),$ $C_1 = N_s(M_{22} \cos \phi - M_{12}n \sin \phi),$ $C_2 = M_{11}n \sin \phi + M_{21} \cos \phi,$ $\phi = 2\pi n t/\lambda.$ $N_s$ is the refractive index of the substrate, and
$\lambda$ is the first wavelength for the first reflectance measurement and the second wavelength for the second reflectance measurement;
and
determining the thickness t and the refractive index n by solving the two reflectance equations.

2. The method of claim 1 wherein the first and second wavelengths of light are selected to be no more than four times the optical thickness of the incremental layer.

3. The method of claim 1 wherein the steps of directing light toward the layer and the base stack further comprise directing the light normal to the surface of the layer.

4. A method of monitoring the thickness t and refractive index n of a thin film layer as the layer is deposited on a base stack of layers, the base stack having a known characteristic matrix M of the form $$M = \begin{pmatrix} M_{11} & iM_{12} \\ iM_{21} & M_{22} \end{pmatrix},$$

comprising the steps of:
directing light at a first wavelength toward the layer and the base stack;
measuring the reflectance of the first wavelength light from the layer and the base stack; p1 directing light at a second wavelength toward the layer and the base stack;
measuring the reflectance of the second wavelength light from the layer and the base stack;
substituting the measured values of reflectance for each wavelength in the relationship $$\text{reflectance} = \frac{(B_1 - C_1)^2 + (B_2 - C_2)^2}{(B_1 + C_1)^2 + (B_2 + C_2)^2}$$

where $B_1 = M_{11} \cos \phi - (M_{21}/n) \sin \phi,$ $B_2 = N_s(M_{12} \cos \phi + (M_{22}/n) \sin \phi),$ $C_1 = N_s(M_{22} \cos \phi - M_{12}n \sin \phi),$ $C_2 = M_{11}n \sin \phi + M_{21} \cos \phi,$ $\phi = 2\pi n t/\lambda.$ $N_s$ is the refractive index of the substrate, and
$\lambda$ is the first wavelength for the first reflectance measurement and the second wavelength for the second reflectance measurement;
determining the thickness t and the refractive index n by solving the two reflectance equations;
updating the characteristic matrix M to include the layer; and
repeating the steps of directing, measuring, deriving, and updating at predetermined increments during the growth of the layer.

5. The method of claim 4 wherein the first and second wavelengths of light are selected to be no more than four times the optical thickness of each measured layer.

6. The method of claim 4 wherein the predetermined measurement increments are selected so that the optical thickness of each measured layer is at least one fourth as large as the first and second wavelengths of light.

7. the method of claim 4 wherein the steps of directing light toward the layer and the base stack further comprise directing the light normal to the surface of the layer.

8. An improved method of making a multiple thin film optical coating which is effective at an operational wavelength, including the steps of calculating the desired thickness and index of refraction for each layer in the coating and deposition each layer while monitoring the thickness and index of refraction of the layer, the improvement comprising:

monitoring the thickness t and refractive index n of each layer as the layer is deposited on a base stack of layers, the base stack having a known characteristic matrix M of the form $$M = \begin{pmatrix} M_{11} & iM_{12} \\ iM_{21} & M_{22} \end{pmatrix},$$

by:

directing light at a first wavelength toward the layer and the base stack;

measuring the reflectance of the first wavelength light from the layer and the base stack;

directing light at a second wavelength toward the layer and the base stack;

measuring the reflectance of the second wavelength light from the layer and the base stack;

substituting the measured values of reflectance for each wavelength in the relationship $$\text{reflectance} = \frac{(B_1 - C_1)^2 + (B_2 - C_2)^2}{(B_1 + C_1)^2 + (B_2 + C_2)^2}$$

where $B_1 = M_{11} \cos \phi - (M_{21}/n) \sin \phi$, $B_2 = N_s(M_{12} \cos \phi + (M_{22}/n) \sin \phi)$, $C_1 = N_s(M_{22} \cos \phi - M_{12}n \sin \phi)$, $C_2 = M_{11}n \sin \phi + M_{21} \cos \phi$, $\phi = 2\pi n t/\lambda$, $N_s$ id the refractive index of the substrate, and $\lambda$ is the first wavelength for the first reflectance measurement and the second wavelength for the second reflectance measurement;

determining the thickness t and the refractive index n by solving the two reflectance equation;

updating the characteristic matrix M to include the layer; and repeating the steps of directing, measuring, deriving, and updating at predetermined increments during the growth of the layer.

9. The method of claim 8 wherein the first and second wavelengths of light are selected to be no more than four times the optical thickness of each measured layer.

10. The method of claim 8 wherein the predetermined measurement increments are selected so that the optical thickness of each measured layer is at least one fourth as large as the first and second wavelengths of light.

11. The method of claim 8 wherein the predetermined measurement increments are selected so that the optical thickness of each measured layer is no more than 1/40 of the operational wavelength for the coating.

12. The method of claim 8 wherein the steps of directing light toward the layer and the base stack further comprise directing the light normal to the surface of the layer.

* * * * *